United States Patent
Tseng et al.

(10) Patent No.: US 8,372,651 B2
(45) Date of Patent: Feb. 12, 2013

(54) METHOD OF MONITORING A SURFACTANT IN A MICROELECTRONIC PROCESS BY ABSORBANCE

(75) Inventors: Amy M. Tseng, Woodridge, IL (US); John E. Hoots, Batavia, IL (US); Brian V. Jenkins, Warrenville, IL (US)

(73) Assignee: Nalco Company, Naperville, IL (US)

( * ) Notice: Subject to any disclaimer, the term of this patent is extended or adjusted under 35 U.S.C. 154(b) by 979 days.

(21) Appl. No.: 11/696,797

(22) Filed: Apr. 5, 2007

(65) Prior Publication Data

US 2008/0245134 A1 Oct. 9, 2008

(51) Int. Cl.
*G01N 21/75* (2006.01)

(52) U.S. Cl. .......... 436/166; 436/55; 436/103; 436/104; 436/163; 436/164; 134/1.3; 134/2; 134/25.4

(58) Field of Classification Search ............ 436/55, 436/103, 104, 163, 164, 166; 134/1.3, 2, 134/25.4
See application file for complete search history.

(56) References Cited

U.S. PATENT DOCUMENTS

| 4,992,380 | A | * | 2/1991 | Moriarty et al. | 436/55 |
| 5,972,862 | A | * | 10/1999 | Torii et al. | 510/175 |
| 6,238,487 | B1 | * | 5/2001 | Jenkins et al. | 134/2 |
| 2005/0037509 | A1 | * | 2/2005 | Geisler et al. | 436/164 |
| 2006/0124586 | A1 | * | 6/2006 | Kobayashi et al. | 216/41 |

OTHER PUBLICATIONS

Al-Kindy et al, "A sequential injection method for the determination of Tween-80 in natural water samples using a fluorescence enhancement of the dye Eosin-B", Analytical Sciences, vol. 19, May 2003, pp. 737-742.*

Scampavia et al.; Micro-Sequential Injection: A multipurpose Lab-on-Valve for the Advancement of Bioanalytical Assays; Analytical Science 2001; vol. 17 Supplement, pp. i429-i430.

Wu et al.; Micro-Sequential Injection: Lab-On-Valve for Process Monitoring and Bioanalytical Assays; Process Analytical Technology; May/Jun. 2006, vol. 3, Issue 3, pp. 25-30.

* cited by examiner

*Primary Examiner* — Dennis M White
(74) *Attorney, Agent, or Firm* — Calfee, Halter & Griswold, LLP

(57) ABSTRACT

A method of monitoring a surfactant in a microelectronic process is disclosed. Specifically, the monitoring of a surfactant occurs by studying the absorbance of a sample collected from a microelectronic process.

31 Claims, No Drawings

METHOD OF MONITORING A SURFACTANT IN A MICROELECTRONIC PROCESS BY ABSORBANCE

FIELD OF THE INVENTION

The invention pertains to monitoring a surfactant that is added to a process for making a microelectronic component.

BACKGROUND

Surfactants play a pivotal role in the manufacturing of microelectronics. For example, during a photolithography process, surfactants are added to photoresist developers to facilitate their distribution across a wafer's surface. Proper distribution of the photoresist developer is crucial to chip configuration. Therefore, a metrology for surfactants is highly desirable. Presently, current microelectronic processes utilize a sonic surface tension measurement as a metrology for surfactant levels. This metrology suffers drawbacks, which includes low sensitivity to changes in surfactant dosages and being operator dependent. A more sensitive metrology and consistent metrology for surfactant levels are thus desired.

Another example of where surfactants are used in a microelectronic process is in the wet-etching stage of wafer manufacturing. Specifically, surfactants facilitate the dispersal of etchants applied to a wafer during an etching process. By doing so, a microelectronics manufacturer can achieve a more uniform and predictable result during the etching process. Precise control of the concentration of surfactant in the etchant can help achieve a more consistent outcome and therefore a need to monitor surfactants added to a microelectronic process is desired.

SUMMARY OF THE INVENTION

The present invention provides for a method of monitoring a surfactant in a process for making a microelectronic component comprising: adding a surfactant to a process for making a microelectronic component, wherein the absorbance of the surfactant is capable of being measured; sampling fluid from the process; measuring the absorbance of the surfactant in the sample; correlating the absorbance of the surfactant in the sample with the concentration of the surfactant in the process; and optionally taking action to maintain the concentration of the surfactant in the process at a desired level.

The present invention also provides for a method of monitoring a surfactant in a process for making a microelectronic component comprising: adding a surfactant to a process for making a microelectronic component; sampling fluid from the process, wherein sampling includes adding a chromogenic agent to the sample and forming a reacted surfactant; measuring at least the absorbance of the reacted surfactant in the sample; correlating the absorbance of the reacted surfactant with the concentration of the surfactant in the process; and optionally taking action to maintain the concentration of the surfactant in the process at a desired level.

DETAILED DESCRIPTION OF THE INVENTION

The above-mentioned methodologies may be applied to various stages of a process for making a microelectronic component.

In one embodiment, the process is a photolithography process.

In another embodiment, the process is a wet-etching process.

Sampling fluid from a microelectronic process can occur via various routes.

In one embodiment, fluid is drawn from a process via a side-stream and the sample is subsequently analyzed in a flow cell.

In another embodiment, fluid is sampled subsequent to the addition of surfactant to the process and before application of the surfactant to a wafer.

During the sampling stage the sample can be prepared for measurement as well.

In one embodiment, sampling includes dilution of the sample and/or removal of contaminants from the sample.

In another embodiment, sampling involves a sequential injection analysis ("SIA") of the sample or a segmented flow analysis ("SFA") of the sample.

SFA and SIA techniques are well known to those of ordinary skill in the art and therefore the integration of an SIA or SFA analysis technique can be accomplished without undue experimentation. With respect to sampling, SIA, for example, allows a reagent, e.g. a chromogenic agent, to be added to sample in an efficient and practical manner. More specifically, SIA provides a method for reducing the amount of a reagent that needs to be added to a sample containing an analyte to provide a given effect that is necessary for analysis of a sample. SIA also involves measurement of the sample.

In another embodiment, sampling involves flow injection analysis ("FIA) of the sample. FIA analysis is known to those of ordinary skill in the art and can be carried out without undue experimentation.

In another embodiment, sampling utilizes a Lab-on-Valve module. In particular, the Lab-on-Valve module is associated with the process for making a microelectronic component. The Lab-on-Valve module serves as a platform upon which a sample can be drawn in, prepared for measurement, e.g. mixing with a reagent, and for implementation of SIA or SFA analysis. An analytical measurement, such as pH of the sample, viscosity of the sample, or conductivity of the sample can be measured with the Lab-on-Valve module. The use of the Lab-on-Valve module in the analytical arts is well known and can be practiced without undue experimentation.

Measuring the absorbance of the surfactant in the sample takes place after the sample is collected, which could be right after the sample is collected, after mixing with a reagent, after manipulation of the sample, or after the sample is prepared in any particular manner that allows absorbance of the surfactant to be directly or indirectly measured.

In one embodiment, the absorbance is ultraviolet visible absorbance.

In another embodiment, the absorbance of the surfactant(s) is directly measured because the absorbance of the surfactant is capable of being measured.

In another embodiment, the absorbance of the surfactant is measured indirectly by a forming a reacted surfactant, which is capable of being measured by absorbance.

The correlation between the absorbance of the surfactant and/or reacted surfactant, and the concentration of the surfactant can be made without undue experimentation.

Monitoring a surfactant can take place on-line.

Monitoring a surfactant can take place at various intervals of time.

In one embodiment, monitoring is continuous, sequential, or at a programmed interval of time.

Various types of surfactants may be utilized during a microelectronic process and therefore, depending on the nature of the surfactant, one or more of the discussed In one embodiment, the surfactant is a cationic surfactant. In a further embodiment, the cationic surfactant is a fluorinated surfactant.

In another embodiment, the surfactant is non-ionic surfactant. In a further embodiment, the non-ionic surfactant is a fluorinated surfactant.

Other types of surfactants may be studied as well, such as an anionic surfactant, an amphoteric surfactant, and a zwitterionic surfactant.

The surfactants may be monitored alone or in combination with one another.

When measuring the absorbance of a surfactant directly or indirectly, one or more process variables may be measured in conjunction with the absorbance measurement.

In one embodiment, the process variable(s) are selected from the group consisting of: pH of said process stream; conductivity of said process stream; viscosity of said process stream; and a combination thereof.

Various types of chromogenic agents can be utilized in this protocol.

In one embodiment, the chromogenic agent is 4,5,6,7-Tetrachloro-2',4',5',7'-tetraiodofluorescein disodium salt.

One or more agents can be added to the sample to adjust the absorbance signal positively or negatively. For example, either signal from the absorbance of the surfactant itself and/or the reacted surfactant can be adjusted either positively or negatively.

In one embodiment, at least one modifying agent positively affects the signal and is a cationic agent selected from the group consisting of: tertiary amines; quaternary amines; tetramethylammonium hydroxide; tetrabutylammonium chloride; cetyltrimethylammonium bromide; and a combination thereof.

In another embodiment, the modifying agent positively affects the signal and is an anionic agent that contains at least one of the following functional groups: sulfonate, carboxylate, or phosphonate.

In another embodiment, if an absorbance signal is weak then an enhancer can be added to the sample to positively augment the absorbance signal associated with the surfactant and/or the reacted surfactant.

An inverse protocol may be applied as well. Specifically a modifying agent that quenches an absorbance signal is added, and then the decrease in absorbance of the surfactant and/or reacted surfactant is correlated with the concentration of the surfactant.

The methodology for enhancing/quenching an absorbance signal can occur via different routes.

In one embodiment, a modifying agent is coupled with a chromogenic agent and then the resulting product is added to a sample potentially containing surfactant and then the absorbance of the sample is measured at a specified wavelength(s).

In another embodiment, a complex containing an enhancer component and a chromogenic component are added to sample potentially containing surfactant and the absorbance of the sample is measured at a specified wavelength(s).

Various types of surfactants, chromogenic agents, and modifying agents may be used in combination with one another.

In one embodiment, the chromogenic agent is 4,5,6,7-Tetrachloro-2',4',5',7'-tetraiodofluorescein disodium salt is added to sample containing non-ionic surfactant. In a further embodiment, a modifying agent can be added to this combination to enhance or quench the signal.

In another embodiment, a modifying agent is coupled with chromogenic agent and then is coupled with a surfactant.

In another embodiment, the chromogenic agent is 4,5,6,7-Tetrachloro-2',4',5',7'-tetraiodofluorescein disodium salt is added to sample containing non-ionic surfactant.

In response to surfactant levels, action can be taken to maintain the concentration of surfactant in the microelectronic process at a desired level. This can be done via a wide variety of mechanisms. For example, a controller could process information from the one or more analytical devices and respond by implementing a predetermined protocol. Moreover, the controller may be in communication with a pumping mechanism that controls the flow of surfactant into the process stream. The use of controller makes on-line monitoring of the process stream.

In another embodiment, after the sample is measured it is then discharged to a drain or a collection container.

The following example is not meant to be limiting and is a prophetic example.

EXAMPLE

With respect to dilution ratio (X:Y), the first number refers to the total volume and the second number refers to primary species of interest being diluted. Therefore, if you dilute Y with X, then the first number would be the total volume of X, the volume of species of interest would be Y, and the volume of diluent species (or carrier fluid) would be X−Y. MAX refers to maximum and MIN refers to minimum.

Example 1

Company A uses Surfactant B in a photolithography process for manufacturing of microelectronic circuits. Surfactant B solution is diluted 200:1 (volume/volume) with Carrier Fluid C and the two solutions are mixed to obtain typical use dosage of Surfactant B. A sample of Solution D (solution of 0.5% vol/vol Surfactant B and 99.5% vol/vol Carrier Fluid C) is withdrawn as a side-stream from the mixing and dilution equipment. Solution D is sampled by SIA equipment and then the sample is drawn into the holding coil of the SIA equipment, the sample is diluted, and a reagent is added/mixed into sample. The sample is then sent through a flowcell where the sample is monitored by UV-visible absorbance, and the dosage of Surfactant B solution is measured (or alternatively dilution ratio of surfactant is determined . . . e.g., 0.5% vol/vol=200:1 dilution ratio or 1.0% vol/vol=100:1 dilution ratio). The SIA equipment sends a electrical signal that is proportional to Surfactant B solution dosage to the dilution dosing and mixing equipment in order to determine whether to add more or less of Surfactant B solution (based on the control method and control limits). The analysis sample is then discharged to drain and a new sample is drawn into the SIA equipment to begin a new analysis cycle. In this example, the Surfactant B solution setpoint is 200:1 dilution (0.5% vol/vol) with an upper control limit of 205:1 dilution (0.0488% vol/vol) and lower control limit of 195:1 dilution (0.513% vol/vol). A series of analysis readings and responses of dilution control system are listed below.

TABLE 1

Surfactant B Solution Dosage (with SIA analysis and dosage control)

| Analysis # | Surfactant B Dilution (vol/vol) | Surfactant B Solution Dosage (vol/vol) | Control Signal Response |
|---|---|---|---|
| 1 | 200:1 | 0.500% | No change |
| 2 | 204:1 | 0.490% | No change |

TABLE 1-continued

Surfactant B Solution Dosage (with SIA analysis and dosage control)

| Analysis # | Surfactant B Dilution (vol/vol) | Surfactant B Solution Dosage (vol/vol) | Control Signal Response |
|---|---|---|---|
| 3 | 203:1 | 0.493% | No change |
| 4 | 206:1 | 0.485% | Surfactant B addition rate increased |
| 5 | 201:1 | 0.498% | No change |
| 6 | 196:1 | 0.510% | No change |
| 7 | 194:1 | 0.515% | Surfactant B addition rate decreased |
| 8 | 197:1 | 0.508% | No change |
| 9 | 200:1 | 0.500% | No change |
| 10 | 198:1 | 0.505% | No change |
| 11 | 193:1 | 0.518% | Surfactant addition rate decreased |
| 12 | 197:1 | 0.508% | No change |
| 13 | 198:1 | 0.505% | No change |
| 14 | 199:1 | 0.503% | No change |
| Average | 199:1 | 0.503% | |
| Max | 206:1 | 0.518% | |
| Min | 193:1 | 0.485% | |
| +/−Sigma | +/−3.7:1 | +/−0.009% | |

Table 1 shows much better control of Surfactant B Solution dosage (dilution average is very close to setpoint: 200:1 (0.500%) vs. 199:1 (0.503%). Maximum (Max) and minimum (Min) values [193:1 (0.518%) and 206:1 (0.485%)] are also very close to control band range of 195:1 (0.513%) to 205:1 (0.488%). Table 2 (monitoring only, without dosage control) shows much higher variability, increased deviation from setpoint and higher Max/lower Min dosage values (as compared to Table 1).

TABLE 2

Surfactant B Solution Dosage (with SIA analysis and no dosage control)

| Analysis # | Surfactant B Dilution (vol/vol) | Surfactant B Solution Dosage (vol/vol) | Control Signal Response |
|---|---|---|---|
| 1 | 200:1 | 0.500% | None |
| 2 | 196:1 | 0.510% | None |
| 3 | 192:1 | 0.521% | None |
| 4 | 185:1 | 0.541% | None |
| 5 | 180:1 | 0.556% | None |
| 6 | 182:1 | 0.549% | None |
| 7 | 195:1 | 0.513% | None |
| 8 | 192:1 | 0.521% | None |
| 9 | 187:1 | 0.535% | None |
| 10 | 195:1 | 0.513% | None |
| 11 | 200:1 | 0.500% | None |
| 12 | 202:1 | 0.495% | None |
| 13 | 201:1 | 0.498% | None |
| 14 | 206:1 | 0.485% | None |
| Average | 194:1 | 0.517% | |
| Max | 206:1 | 0.556% | |
| Min | 180:1 | 0.485% | |
| +/−Sigma | +/−7.9:1 | +/−0.021% | |

The invention claimed is:

1. A method of monitoring a surfactant in a process for making a microelectronic component comprising:
   a. adding the surfactant to a process for making a microelectronic component, wherein an absorbance of the surfactant is capable of being measured, wherein the absorbance is ultraviolet-visible absorbance;
   b. sampling fluid from the process;
   c. measuring the absorbance of the surfactant in the sample;
   d. correlating the absorbance of the surfactant in the sample with the concentration of the surfactant in the process; and
   e. taking action to maintain the concentration of the surfactant in the process at a desired level, wherein the desired level is a dilution ratio of about 200 parts total volume to about one part surfactant volume;
   wherein the sampling comprises adding a chromogenic agent into the fluid, the chromogenic agent comprising 4,5,6,7-Tetrachloro-2',4',5',7'-tetraiodofluorescein disodium salt.

2. The method of claim 1 wherein the process is a photolithography process.

3. The method of claim 1 wherein the process is a wet-etching process.

4. The method of claim 1 wherein the process is monitored on-line.

5. The method of claim 1 wherein the sampling involves an SIA analysis of the sample or an SFA analysis of the sample.

6. The method of claim 1 wherein sampling uses a LOV module for a sample analysis.

7. The method of claim 1 wherein sampling includes dilution of the sample and/or removal of contaminants from the sample.

8. The method of claim 1 wherein the surfactant is a cationic surfactant.

9. The method of claim 8 wherein the surfactant is a fluorinated surfactant.

10. The method of claim 1 wherein the surfactant is a non-ionic surfactant.

11. The method of claim 10 wherein the surfactant is a fluorinated surfactant.

12. The method on claim 1 wherein the monitoring is continuous, sequential, or at a programmed interval.

13. The method of claim 1 wherein sampling includes measuring an additional process variable, optionally wherein the process variable includes at least one of the following process variables: pH of the process; conductivity of the process stream; and viscosity of the process stream.

14. The method of claim 1 wherein the process is monitored on-line.

15. A method of monitoring a surfactant in a process for making a microelectronic component comprising:
   a. adding the surfactant to a process for making a microelectronic component;
   b. sampling fluid from the process, the sampling performed subsequent to the addition of the surfactant to the process and also before application of the surfactant to the microelectronic component, the sampling accomplished by drawing the sample into a side stream comprising a flow cell, wherein the sampling includes comprises adding a chromogenic agent to the sample and forming a reacted surfactant;
   c. measuring an absorbance of the reacted surfactant in the sample, wherein the absorbance is ultraviolet-visible absorbance;
   d. correlating the absorbance of the reacted surfactant with the concentration of the surfactant in the process;
   e. taking action to maintain the concentration of the surfactant in the process at a desired level; wherein the desired level is a dilution ratio of about 200 parts total volume to about one part surfactant volume; and
   wherein the chromogenic agent is 4,5,6,7-Tetrachloro-2',4',5',7'-tetraiodofluorescein disodium salt.

16. The method of claim 15 further comprising adding at least one modifying agent to the sample, which modifies the absorbance signal of the surfactant positively or negatively.

17. The method of claim 16 wherein said modifying agent positively affects the signal and is a cationic agent selected from the group consisting of: tertiary amines; quaternary amines; tetramethylammonium hydroxide; tetrabutylammonium chloride; cetyltrimethylammonium bromide; and a combination thereof.

18. The method of claim 16 wherein the modifying agent positively affects the signal and is an anionic agent that contains at least one of the following functional groups: sulfonate, carboxylate, and phosphonate.

19. The method of claim 16 wherein said surfactant is a non-ionic surfactant.

20. The method of claim 15 wherein said surfactant is a cationic surfactant.

21. The method of claim 20 wherein the surfactant is a fluorinated surfactant.

22. The method of claim 15 wherein said surfactant is a non-ionic surfactant.

23. The method of claim 22 wherein the surfactant is a fluorinated surfactant.

24. The method of claim 15 wherein the process is a photolithography process.

25. The method of claim 15 wherein the process is a wet-etching process.

26. The method of claim 15 wherein the process is monitored on-line.

27. The method of claim 15 wherein the sampling involves an SIA analysis of the sample or an SFA analysis of the sample.

28. The method of claim 15 wherein sampling uses a LOV module for a sample analysis.

29. The method of claim 15 wherein sampling includes dilution of the sample and/or removal of contaminants from the sample.

30. The method on claim 15 wherein the monitoring is continuous, sequential, or at a programmed interval.

31. The method of claim 15 wherein sampling includes measuring an additional process variable, optionally wherein the process variable includes at least one of the following process variables: pH of the process; conductivity of the process stream; and viscosity of the process stream.

* * * * *